(12) United States Patent
Goebel

(10) Patent No.: US 11,446,454 B2
(45) Date of Patent: Sep. 20, 2022

(54) DEVICE FOR RESPIRATORY THERAPY

(71) Applicant: Loewenstein Medical Technology S.A., Luxembourg (LU)

(72) Inventor: Christof Goebel, Hamburg (DE)

(73) Assignee: LOEWENSTEIN MEDICAL TECHNOLOGY S.A., Luxembourg (LU)

(*) Notice: Subject to any disclaimer, the term of this patent is extended or adjusted under 35 U.S.C. 154(b) by 924 days.

(21) Appl. No.: 16/177,508

(22) Filed: Nov. 1, 2018

(65) Prior Publication Data

US 2019/0151581 A1 May 23, 2019

(30) Foreign Application Priority Data

Nov. 3, 2017 (DE) .......................... 102017010225.2

(51) Int. Cl.
| | | |
|---|---|---|
| *A61M 16/00* | (2006.01) | |
| *A61M 16/20* | (2006.01) | |
| *A61M 16/06* | (2006.01) | |
| *A61M 16/10* | (2006.01) | |

(52) U.S. Cl.
CPC .... *A61M 16/0009* (2014.02); *A61M 16/0006* (2014.02); *A61M 16/0096* (2013.01); *A61M 16/06* (2013.01); *A61M 16/105* (2013.01); *A61M 16/202* (2014.02); *A61M 16/20* (2013.01); *A61M 16/203* (2014.02); *A61M 2016/003* (2013.01); *A61M 2016/0027* (2013.01)

(58) Field of Classification Search
CPC ............ A61M 16/0006; A61M 16/202; A61M 16/0009; A61M 16/0066; A61M 16/20–203; F16K 11/0716; F16K 11/076; F16K 11/0856
See application file for complete search history.

(56) References Cited

U.S. PATENT DOCUMENTS

| | | | |
|---|---|---|---|
| 6,209,540 B1* | 4/2001 | Sugiura ............. | A61M 16/0006 128/205.24 |
| 2003/0078512 A1* | 4/2003 | Jonson ................ | A61M 16/026 600/538 |
| 2007/0186928 A1* | 8/2007 | Be'Eri .............. | A61M 16/0009 128/204.21 |

(Continued)

FOREIGN PATENT DOCUMENTS

| | | |
|---|---|---|
| DE | 19914749 A1 | 12/1999 |
| WO | 2017144963 A2 | 8/2017 |

*Primary Examiner* — Joseph D. Boecker
*Assistant Examiner* — Thomas W Greig
(74) *Attorney, Agent, or Firm* — Abel Schillinger, LLP

(57) ABSTRACT

The present invention relates to a respiratory therapy device (1) for the targeted assistance of a secretion removal from the airways of a patient and a method for operating such a respiratory therapy device (1). The respiratory therapy device (1) comprises a flow unit (2) for generating a respiratory airflow for an insufflation and a respiratory airflow for an exsufflation, which comprises a patient interface (3) for connecting the patient and a respiratory air interface and two fans (5, 6) fluidically connected in parallel each having an intake side (15, 16) and a delivery side (25, 26). A first fan (5) is fluidically coupled with its intake side (15) and a second fan (6) is fluidically coupled with its delivery side (26) to a switchable valve unit (7).

20 Claims, 4 Drawing Sheets

(56) References Cited

U.S. PATENT DOCUMENTS

| | | | |
|---|---|---|---|
| 2012/0285460 A1* | 11/2012 | Smith | A61M 16/0069 128/205.24 |
| 2014/0290659 A1* | 10/2014 | Chen | A61M 16/20 128/205.24 |
| 2016/0151232 A1* | 6/2016 | Clapp | A61H 9/0078 601/148 |
| 2019/0298947 A1* | 10/2019 | Trivikram | A61H 9/0078 |

* cited by examiner

DEVICE FOR RESPIRATORY THERAPY

CROSS-REFERENCE TO RELATED APPLICATIONS

The present application claims priority under 35 U.S.C. § 119 of German Patent Application No. 102017010225.2, filed on Nov. 3, 2017, the entire disclosure of which is expressly incorporated by reference herein.

BACKGROUND OF THE INVENTION

1. Field of the Invention

The present invention relates to a respiratory therapy device, in particular a coughing device, for the targeted assistance of a secretion removal from the airways of a patient. The respiratory therapy device comprises at least one flow unit for generating at least one respiratory airflow for an insufflation into the patient and for generating at least one respiratory airflow for an exsufflation out of the patient.

2. Discussion of Background Information

In certain illnesses, a direct or indirect impairment of the secretion removal from the airways and/or the lungs occurs. To enable and/or intentionally assist a secretion removal in such patients, so-called coughing devices or coughing machines can be used.

In healthy people, the secretion can generally be removed by coughing. During the coughing process, after inhalation, a sudden and forceful exhalation movement occurs. A very rapid airflow arises in this case, using which the secretion can be expelled.

The coughing devices can assist and/or partially emulate this coughing process by way of a targeted respiratory airflow. For this purpose, respiratory air is generally firstly blown into the lungs, the so-called insufflation, and subsequently drawn out again, the so-called exsufflation. In this case, the coughing device is to be capable of causing the exsufflation to follow as rapidly and suddenly as possible on the insufflation. Furthermore, it is decisive that appropriately high flow speeds for the exsufflation can be generated using the coughing device.

Therefore, the demands on a respiratory therapy device designed as a coughing device differ substantially from the demands and options which are known from respirators.

The known coughing devices generally operate reliably. However, an improvement of these devices is advantageous to be able to offer still more effective and/or more pleasant assistance to the patient during the secretion removal. Moreover, the use of the known coughing devices is often linked to correspondingly high cost.

SUMMARY OF THE INVENTION

It would therefore be advantageous to have a respiratory therapy device available which enables particularly effective and preferably also more pleasant assistance of a secretion removal from the airways of a patient. In particular, particularly cost-effective production of the respiratory therapy device is also to be possible.

The present invention provides a respiratory therapy device having the features of the independent claims. Preferred refinements are the subject matter of the dependent claims. Further advantages and features of the present invention result from the general description and the description of the exemplary embodiments.

The respiratory therapy device according to the invention is, for example, a coughing device and is used for the targeted assistance of secretion removal from the airways of a patient using at least one flow unit. The respiratory therapy device according to the invention is designed, for example, also as a combined coughing device and respirator or as a respirator. The flow unit is used for generating at least one respiratory airflow for an insufflation into the patient and for generating at least one respiratory airflow for an exsufflation out of the patient. The terms insufflation and exsufflation are also used synonymously in the meaning of the present invention for the inspiration and expiration, respectively (in the scope of breathing). The flow unit comprises at least one patient interface for connecting the patient to the respiratory therapy device. The flow unit comprises at least one respiratory air interface for connecting the respiratory therapy device to the respiratory air and/or ambient air. The connection is to be understood in the meaning of the invention in particular as establishing an air-conducting or pneumatic connection. In this case, the flow unit comprises at least two flow paths extending in parallel, each having at least one intake side and at least one delivery side. In this case, the flow unit comprises at least one gas source in each of the flow paths, for example, designed as a fan, each having at least one intake side and at least one delivery side. At least one first fan is fluidically coupled with its intake side and at least one second fan is fluidically coupled with its delivery side to at least one switchable valve unit.

The gas sources, for example, the fans, are arranged inversely in relation to one another in the flow paths, for example, whereby they can generate respiratory airflows opposing one another, for example. The gas sources can be designed, for example, as one fan and one valve or as two fans or as two valves. According to the invention, a plurality of gas sources can also be provided.

According to the invention, the term insufflation is understood in particular as aerating or filling of the lungs. An insufflation comprises in particular an air supply or an inspiration in the scope of an inhalation process or a respiration.

According to the invention, the term exsufflation is understood in particular as deaerating of the lungs. An exsufflation comprises in particular an expiration or an air discharge in the scope of an exhalation process or a respiration.

The respiratory therapy device according to the invention offers many advantages. One substantial advantage is that two fans connected in parallel are provided. The switchable valve unit, which is coupled accordingly to the fans, is also particularly advantageous. A particularly rapid reversal of the volume flow or flow and/or the pressure can thus be implemented.

It is thus possible to change very rapidly between the insufflation and the exsufflation. Moreover, the insufflation and exsufflation can thus also be adapted very individually to the needs of the patient. The insufflation and exsufflation are thus also settable particularly accurately in time and exactly. This is also advantageous, for example, in the case of a particularly soft assistance. The respiratory therapy device according to the invention therefore offers a particularly effective and also very pleasant assistance for the secretion removal.

Because of the at least two fans, it is possible to change substantially more quickly between insufflation and exsufflation, since it is not first necessary to wait for a speed adaptation or the like. Using the valve unit, it is then possible to switch rapidly from one fan to the other, while, for example, a speed of the fans was already set appropriately beforehand.

The switchable valve unit moreover offers the advantage that two separate flow paths, one for each of the fans, can be dispensed with. The design expenditure is thus optimized, so that the respiratory therapy device according to the invention is producible cost-effectively and enables an economical secretion therapy.

In particular, the at least two fans comprise at least one first fan and at least one second fan. In particular, the two fans are operable independently of one another and are preferably controllable independently of one another.

In the scope of the present invention, a control or a controller is preferably also understood as a regulation or a regulator. The flow unit in particular comprises at least one control unit for controlling the fans and/or the valve unit. In the scope of the present invention, a connection is preferably also understood as a fluidic connection or flow connection.

The valve unit is preferably suitable and designed for the purpose of fluidically connecting either the first fan or the second fan to the respiratory air interface depending on the valve position. The valve unit can also be suitable and designed for the purpose of connecting either the first fan or the second fan to the patient interface depending on the valve position. Thus, depending on the valve position, the respiratory airflow can be supplied to the patient for the insufflation or guided away from the patient for the exsufflation, respectively.

The respiratory airflow for the insufflation thus in particular has a reverse flow direction to the respiratory airflow for the exsufflation. In particular, by switching over the valve unit, the flow direction of the respiratory airflow is reversible in that either the first or the second fan is switched on.

The valve unit is preferably fluidically arranged between the at least two fans and the respiratory air interface. The valve unit can also be fluidically arranged between the at least two fans and the patient interface. Such positions for the valve unit enable a particularly rapid change between insufflation and exsufflation and are implementable with particularly simple design.

The at least two fans are preferably simultaneously fluidically connected to the patient interface or the patient if the valve unit is fluidically arranged between the at least two fans and the respiratory air interface. Preferably, either the first fan or the second fan is connected to the respiratory air interface in dependence on a valve position if the valve unit is arranged between the fans and the respiratory air interface. This has the advantage that the respiratory air interface only has to be connected to the corresponding fan for the change between insufflation and exsufflation.

The respective fan not connected to the respiratory air interface is in particular not active toward the patient in the sense of air delivery and buildup of overpressure or partial vacuum, respectively, in the respective phase, since the inflow toward this fan or outflow away from this fan, respectively, is completely or at least substantially suppressed by the valve unit.

The at least two fans are preferably simultaneously fluidically connected to the respiratory air interface, if the valve unit is fluidically arranged between the at least two fans and the patient interface. Preferably, either the first fan or the second fan is connected to the patient interface in dependence on a valve position, if the valve unit is arranged between the at least two fans and the patient interface. This has the advantage that the patient interface only has to be connected to the corresponding fan for the change between insufflation and exsufflation.

The valve unit is preferably suitable and designed for the purpose of connecting the intake side of the first fan to the respiratory air interface or to the patient interface and blocking the delivery side of the second fan in at least one first valve position.

The valve unit is preferably suitable and designed for the purpose of connecting the intake side of the first fan to the respiratory air interface in the first valve position, if the valve unit is fluidically arranged between the fans and the respiratory air interface. In this case, respiratory air is in particular drawn in and blown into the patient using the first fan. The valve unit can also be suitable and designed for the purpose of connecting the intake side of the first fan to the patient interface in the first valve position if the valve unit is fluidically arranged between the fans and the patient interface. In this case, air is in particular drawn out of the patient and blown out of the device using the first fan.

The valve unit is preferably suitable and designed for the purpose of blocking the intake side of the first fan and connecting the delivery side of the second fan to the respiratory air interface or to the patient interface in at least one second valve position.

The valve unit is preferably suitable and designed for the purpose of connecting the delivery side of the second fan to the respiratory air interface in the second valve position if the valve unit is fluidically arranged between the fans and the respiratory air interface. In this case, air is in particular drawn out of the patient and blown out of the device using the second fan. The valve unit can also be suitable and designed for the purpose of connecting the delivery side of the second fan to the patient interface in the second valve position if the valve unit is fluidically arranged between the fans and the patient interface. In this case, respiratory air is in particular drawn in and blown toward the patient interface or into the patient using the second fan.

The valve unit is in particular suitable and designed for the purpose of blocking the intake side of the first fan and blocking the delivery side of the second fan in at least one third valve position. In the third valve position, in particular neither of the two fans is fluidically connected to the respiratory air interface if the valve unit is arranged between the fans and the respiratory air interface. In the third valve position, the patient interface is in particular fluidically connected to neither of the two fans if the valve unit is arranged between the fans and the patient interface.

Such valve positions offer an option having particularly simple design in order to be able to change very rapidly between insufflation and exsufflation. Leaks are possible and can be intended in all valve positions.

In particular, at least one intermediate position is settable in the first and/or second and/or third valve position. In particular, a valve position comprises various degrees of opening. The intermediate position comprises in particular a degree of opening which lies between completely open and completely closed. In particular, at least one fitting of the valve unit can be completely open and completely closed in the first and/or second and/or third valve position and can preferably also be moved into a degree of opening located therebetween.

In one particularly preferred embodiment, the valve unit comprises at least one 3/3-directional valve. Such a valve operates particularly reliably and dependably and offers a particularly cost-effective embodiment. The directional valve preferably comprises at least three fittings. In particular, the directional valve comprises at least three valve positions. The directional valve particularly preferably comprises the first and the second and the third valve position. In particular, the directional valve comprises at least one fitting for the intake side of the first fan and at least one fitting for the delivery side of the second fan and at least one fitting for the respiratory air interface or patient interface.

The valve unit can also comprise a directional valve having more valve positions and/or more fittings. Fewer valve positions and/or fewer fittings are also possible.

The valve unit is preferably designed as a proportional valve or comprises at least one such valve. A proportional valve enables a particularly targeted adaptation of the insufflation and/or exsufflation to the needs of the patient. It offers, for example, very rapid and at the same time particularly pleasant transitions. The valve unit can also comprise a valve having discrete valve positions or can be designed as such a valve.

The valve unit is particularly preferably designed as a 3/3-directional-proportional valve. The proportional valve is in particular a valve in which a result at a fitting or outlet can be changed proportionally to a value at another fitting or at the inlet. In particular, the result at the first and/or second fitting can be changed proportionally to the value at the third fitting. Whether the result at the first or second fitting is changeable is preferably dependent on whether the first or second valve position is assumed and/or whether the first or second fitting is connected to the third fitting.

In particular, the proportional valve comprises at least three fittings. In particular, in the case of an at least partially open first fitting, a second fitting is always closed. In particular, in the case of an at least partially open second fitting, the first fitting is always closed. This has the advantage that the flow rate at one fitting is settable, while the flow rate at the other fitting can be completely blocked. In this case, leaks are possible and can be intended. The first fitting and the second fitting are preferably each connected to one fan. A third fitting is preferably used as an inlet and/or outlet for the other fittings. The third fitting is preferably always open. The third fitting can also be designed as closable and/or openable. The third fitting is preferably connected to the patient interface or to the respiratory interface.

It is also possible and preferable that in the case of an at least partially open first fitting, a second fitting is at least partially open and/or vice versa. It is possible that the opening at one fitting merges into an opening at the other fitting. The valve can be designed for this purpose, for example, as a rotary slide valve. The rotary slide valve is then designed, for example, such that one behavior results for one rotational direction and the other behavior results for the other rotational direction. In such a case, at least two openings of the rotary slide valve on the circumference of the valve body are not distributed uniformly in the angle positions thereof.

The proportional valve is preferably suitable and designed for the purpose of setting a flow rate for the respiratory airflow for the insufflation to an amount between a maximum flow rate and a blocked flow rate and at the same time to block a flow rate for the respiratory airflow for the exsufflation. It is also possible that the proportional valve is suitable and designed for the purpose of setting a flow rate for the respiratory airflow for the exsufflation to an amount between a maximum flow rate and a blocked flow rate and at the same time blocking a flow rate for the respiratory airflow for the insufflation. For example, a defined valve opening for the intake side of the first fan can thus be set, while the delivery side of the second fan is blocked.

It is preferable for the valve unit to comprise at least one rotary slide valve or to be designed as such a valve. A rotary slide valve can implement the required valve positions particularly advantageously, since it operates reliably, can be activated very accurately, and is cost-effective. The rotary slide valve is designed in particular as a 3/3-directional valve. The rotary slide valve is designed in particular as a proportional valve. The rotary slide valve in particular provides the 3/3-directional valve and/or the proportional valve. The rotary slide valve is driven in particular by a stepping motor.

The valve positions are in particular each implementable by at least one axial rotation of a valve piston. In particular, the fittings for the fans are arranged radially and/or transversely in relation to the axis of rotation of the valve piston. In particular, a fitting for the respiratory air interface and/or for the patient interface is arranged axially and/or parallel in relation to the axis of rotation of the valve piston. Other arrangements of the fittings are also possible. The fittings for the fans are opposite to one another in particular. The fittings of the fans can also be arranged at another suitable angle in relation to one another.

In particular, at least one drive unit for rotating the valve piston is arranged axially and/or parallel to the axis of rotation of the valve piston. The drive unit can also be arranged radially and/or transversely to the axis of rotation or in another suitable position in relation to the valve unit.

The valve piston in particular has at least one channel, which is connectable to at least one of the fittings of the rotary slide valve by way of a rotation of the valve piston. The channel comprises in particular at least two channel openings, wherein at least one channel opening is arranged radially and at least one channel opening is arranged axially on the valve piston. Other arrangements are also possible. It is possible that the channel is only connectable to one of the radial fittings in each case at a given point in time. It can also be provided that the channel is connectable simultaneously to at least two radial fittings. For example, it can be provided that the opening partially overlaps two fittings simultaneously.

It is possible that the fittings of the rotary slide valve are distributed asymmetrically and/or not opposing in relation to a circumference of the valve piston. In this case, the valve piston can preferably be moved in two rotational directions. In particular, the channel of the valve piston can be connected to the fitting in the one rotational direction via a first longer path and in the other rotational direction via a second shorter path. This has the advantage that a different behavior results for the one rotational direction than for the other rotational direction. A constructively simple and also very effective setting of the flow dynamics and/or the dynamics of the respiratory therapy can thus be performed.

Preferably, a complete and in particular longer closing of the fitting takes place via the first path. It is possible that the fitting remains partially open via the second path, or a shorter closing of the fitting takes place via the second path. For example, a rotational angle of 270° is associated with the first path and a rotational angle of 90° is associated with the second path. Other rotational angles are also possible.

However, it is also possible and preferable for the fittings of the rotary slide valve to be distributed symmetrically and/or opposing in relation to a circumference of the valve piston.

The valve unit can also comprise at least one valve having displaceable pistons and/or another suitable switchable valve construction.

In one preferred refinement, the flow unit is suitable and designed for the purpose of also operating at least one of the at least two fans if the intake side or delivery side of the fan is blocked by the valve unit. In particular, at least one of the at least two fans is operable independently of the valve position. The advantages of the combination of at least two fans and at least one valve unit can thus be utilized particularly well. For example, one fan can be activated and set before it is switched in by the valve unit or after it has been blocked by the valve unit.

The flow unit is particularly preferably suitable and designed for the purpose of setting a requested operating point of at least one of the at least two fans, while the intake side or delivery side of the fan to be set is blocked by the valve unit. The fan thus has already reached the requested speed when it is switched in. A particularly rapid change of insufflation and exsufflation is thus possible and the coughing can be assisted particularly effectively. The operating point defines in particular a speed and/or a voltage and/or at least one other characteristic parameter for a setting of the fan. The setting comprises, for example, lowering and/or raising the speed.

It can also be provided that the flow unit is suitable and designed for the purpose of setting the requested operating point and, for example, a requested speed and/or voltage of at least one of the at least two fans when the valve unit has already connected the fan to be set to the respiratory air interface or patient interface. This enables a particularly targeted setting to the needs of the patient.

It is possible that the respiratory therapy device comprises at least one oscillator unit. The oscillator unit is used in particular to apply at least one defined oscillation of at least one of the variables flow and/or pressure to the respiratory airflow for the insufflation and/or exsufflation. Solidly fixed secretion can be detached particularly well by such an oscillator unit.

The defined oscillation is preferably a pressure oscillation and/or a flow oscillation of the respiratory airflow. The defined oscillation is preferably settable. Preferably, a frequency and/or an amplitude and/or another characteristic parameter for the definition of an oscillation is settable. The amplitude can relate to the pressure and/or the volume flow or flow of the respiratory airflow. The amplitude is settable, for example, by a defined degree of opening of the valve unit. The frequency is settable, for example, by a switching frequency of the valve unit. It is possible that the frequency and/or amplitude is settable for the pressure and/or the flow of the respiratory airflow.

The oscillator unit is preferably suitable and designed for the purpose of generating the oscillation by repeated switching over of the valve unit. Costs and components can thus be saved, since the valve unit is already provided. In particular, the oscillator unit is suitable and designed for the purpose of generating the oscillation by at least partially opening and at least partially closing the valve unit. In such an embodiment, the valve unit is preferably designed as a rotary slide valve. The oscillator unit is then in particular suitable and designed for the purpose of generating the oscillation by a repeated rotation of at least one valve piston of the rotary slide valve in various directions. In this case, the rotational movement can take place between the first and second and in particular also the third valve position. However, it is also possible that the rotational movement only takes place within the first and/or second valve position.

It is also possible that the oscillator unit generates the oscillation using another suitable unit. For example, the oscillator unit can comprise at least one rotatable perforated disk for this purpose, which is arranged in the respiratory airflow.

The oscillator unit is preferably suitable and designed for the purpose of switching over the valve unit between a completely open valve position and a partially open valve position during the insufflation and/or the exsufflation. The oscillator unit is preferably suitable and designed for the purpose of switching over the valve unit between a fully open valve position and a fully closed valve position and/or switching over the valve unit between at least two at least partially open valve positions during the insufflation and/or the exsufflation.

The oscillator unit is in particular suitable and designed for the purpose of switching over the valve unit between a fully open and a completely closed valve position during the insufflation and/or the exsufflation. The oscillator unit is in particular suitable and designed for the purpose of switching over the valve unit between one partially open and another partially open valve position or a completely closed valve position during the insufflation and/or the exsufflation.

The oscillator unit is preferably suitable and designed for the purpose of switching over the valve unit between an at least partially open valve position for the insufflation and an at least partially open valve position for the exsufflation during the insufflation. The oscillator unit is preferably suitable and designed for the purpose of switching over the valve unit between an at least partially open valve position for the exsufflation and an at least partially open valve position for the insufflation during the exsufflation. A particularly rapid pressure setting can thus be performed and/or an adaptation of the amplitude of the oscillation can be performed. For example, a particularly rapid and/or pronounced pressure dissipation can take place during the insufflation when a switch is temporarily made into the valve position for exsufflation.

In particular, the oscillator unit is suitable and designed for the purpose of repeatedly switching from the first fan to the second fan and vice versa. The first fan is particularly preferably switched in with a completely open valve position in this case and the second fan is switched in with an only partially open valve position and/or vice versa. In particular, the oscillator unit is suitable and designed for the purpose of switching over between respiratory airflows having a different flow direction in each case.

The oscillator unit is preferably suitable and designed for the purpose of switching over the valve unit between a completely open first and/or second valve position and an at least partially open second and/or first valve position. In particular, a switchover between the first and the second valve position takes place for the oscillation. In this case, it is possible to switch into an intermediate position in the first and/or second valve position.

The switching over in the scope of the oscillation can thus take place, for example, within the first and/or second valve position or, for example, from the first into the second valve position. A particularly effective oscillation can thus be generated.

It is possible and preferable for the oscillator unit to be suitable and designed for the purpose of setting a different maximum and/or minimum degree of opening of the valve unit during the insufflation than during the exsufflation. The oscillations can thus be set particularly individually for the insufflation and exsufflation. For example, switching over between a fully open and a partially open valve position takes place during the insufflation and switching over between a partially open and another partially open valve position takes place during the exsufflation.

The oscillator unit is preferably suitable and designed for the purpose of switching over the valve unit at a frequency of 0.1 Hz to 100 Hz to generate the oscillation during the insufflation and/or exsufflation. The oscillator unit is particularly preferably suitable and designed for the purpose of switching over the valve unit at a frequency of 1 Hz to 30 Hz. Such frequencies enable particularly effective detachment of the secretion. Other frequency ranges are also possible. At least one valve piston of the valve unit is particularly preferably movable and in particular rotatable at this frequency. In particular, the rotary slide valve is suitable and designed for the purpose of executing a rotational direction change of a valve piston at such a frequency.

In one preferred embodiment, the oscillator unit is suitable and designed for the purpose of setting a different frequency and/or amplitude for the oscillation during the insufflation than for the oscillation during the exsufflation. It is also possible that the same frequency and/or amplitude is settable for the insufflation and the exsufflation.

The oscillation can be settable by a user input. For example, the frequency and/or amplitude can be adapted according to user specifications. The settings can preferably be performable separately for the insufflation and the exsufflation.

In one advantageous embodiment, the respiratory air interface comprises at least one air inlet and at least one air outlet. The air inlet and the air outlet are preferably provided by a common opening. This enables a particularly space-saving housing of the respiratory air interface. It is also particularly advantageous that existing device structures having a single opening can be reused. For example, respirators can thus be modified with little effort to form very high-quality and effective coughing devices.

Such an embodiment is particularly advantageous if the valve unit is fluidically arranged between the at least two fans and the respiratory air interface. The selection as to whether drawing in or blowing out is performed through the common opening can then be performed by the valve position. Since simultaneous drawing in and blowing out is thus not provided, unintentional drawing in of blown-out air can be prevented very reliably.

In an embodiment which is also preferred, the patient interface comprises at least one coupling unit for connecting at least one hose unit. The hose unit is connectable to at least one respiratory opening of the patient. The hose unit comprises at least one inhalation hose and at least one exhalation hose. The hose unit can also only comprise at least one inhalation hose. In particular, no exhalation hose is then provided. Such hose units enable a particularly good assistance during the secretion removal. The respiratory therapy device can comprise at least one hose unit.

For example, the hose unit can be designed as a leakage hose system, which is characterized by the integration of at least one leakage opening. The hose unit can also be equipped with at least one valve, which is switchable during exhalation and/or coughing.

In particular, the at least two fans are fluidically connected to the patient interface. This enables a common coupling unit for both fans. The respiratory airflow can then be provided for the insufflation or for the exsufflation at the coupling unit, for example, depending on the valve position.

It is also possible that at least one coupling unit is provided for each of the first and the second fans. The first fan is then separately connected to the exhalation hose and the second fan to the inhalation hose or vice versa, for example.

The flow unit is preferably suitable and designed for the purpose of setting at least one respiratory airflow having at least one defined positive therapy pressure for assisting the breathing for a defined time by means of the valve unit and/or by means of at least one of the at least two fans following the respiratory airflow for the exsufflation. This enables a recovery pause, which is very pleasant for the patient, between the coughing processes. In particular, the flow unit is suitable and designed for the purpose of setting at least one respiratory airflow for breathing following the respiratory airflow for the exsufflation. The patient can thus remain connected to the coughing device and breathe further.

The flow unit can be suitable and designed for the purpose of generating a respiratory airflow having at least one pressure profile.

In particular, the flow unit is suitable and designed for the purpose of setting a respiratory airflow having a PEEP (Positive End-Expiratory Pressure) and/or having a CPAP (Continuous Positive Airway Pressure) for the defined positive therapy pressure. The respiratory airflow having the PEEP and/or CPAP during the pause is particularly helpful for the breathing.

In particular, the respiratory airflow for the positive therapy pressure and preferably for the PEEP and/or CPAP is generated using the fan which is provided for generating the respiratory airflow for the insufflation. This fan is in particular switched in by the valve unit when the respiratory airflow for the dynamic pressure is generated. At least one speed adaptation of at least one of the at least two fans is preferably performed to generate the positive therapy pressure.

In particular, a lower volume flow and/or pressure is provided for the positive therapy pressure and preferably for the PEEP and/or the CPAP than for the insufflation. The volume flow and/or pressure of the respiratory airflow for the positive therapy pressure is, for example, less than half of the volume flow and/or pressure of the respiratory airflow for the insufflation.

It is possible that the respiratory therapy device comprises at least one respiration unit. The respiration unit is in particular suitable and designed for the purpose of generating a respiratory airflow for the respiration of the patient by means of the flow unit. Such an embodiment is particularly advantageous, since the respiratory therapy device can also be used for a respiration of the patient, in addition to assisting the secretion removal. Patients often require an assistance during the secretion removal in combination with a respiration. These objects can be provided by a single device by way of the integration of a respiration unit in the respiratory therapy device according to the invention. Moreover, the respiratory therapy device can be integrated particularly simply into an existing respirator. An existing respirator can also be integrated particularly simply into the respiratory therapy device.

The respiration unit comprises in particular at least one control unit for controlling the flow unit and/or for setting respiration parameters. The respiration unit and the flow unit can also have at least one common control unit. The control unit comprises, for example, at least one processor and/or controller and/or at least one algorithm and/or a piece of software.

The respiration unit is in particular suitable and designed for the purpose of generating a respiratory airflow for inspiration and/or for expiration and/or a positive therapy pressure by means of the flow unit. In particular, the respiration unit is suitable and designed for the purpose of using the respiratory airflow for the insufflation as the respiratory airflow for the inspiration and/or for the respiration of the patient by means of the flow unit. A device having such a respiration unit enables a respiration which can be adapted particularly well to the needs of the patient.

In one such embodiment, the patient interface can particularly preferably be coupled to at least one hose unit for the respiration. For example, a hose unit for leakage respiration and/or valve respiration can be provided.

The respiration unit is preferably suitable and designed for the purpose of generating a negative therapy pressure in the scope of a respiration, so that an exhalation process can be assisted with a partial vacuum. The exhaled air can thus be discharged more rapidly and/or the exhalation can take place significantly more easily for the patient. One particular advantage of this is that secretion can thus be detached and/or discharged, without coughing being necessary. This substantially reduces the strain to the patient. Thus, for example, a secretion aid is possible in the scope of respiration which is overall normal per se. Such an embodiment can be implemented particularly advantageously on the basis of the two fans connected in parallel and/or the switchable valve unit coupled thereon.

The negative therapy pressure corresponds in particular to a partial vacuum at the patient interface and/or in the hose unit and/or in the airways of the patient. The negative therapy pressure is characterized in particular by at least one increase of the peak flows. The negative therapy pressure is generated in particular using the fan and/or using the valve position, which is also provided for generating the respiratory airflow for the exsufflation. A different generation of the negative therapy pressure is also possible.

In the above-mentioned embodiment, the patient interface can preferably be coupled to at least one hose unit, which comprises at least one inhalation hose and at least one exhalation hose.

The respiratory airflow for the insufflation can particularly be generated by the first fan and/or the respiratory airflow for the exsufflation can particularly be generated by the second fan. It is also possible that the respiratory airflow for the insufflation can be generated by the second fan and/or the respiratory airflow for the exsufflation can be generated by the first fan.

The method according to the invention is used for operating a respiratory therapy device for the targeted assistance of a secretion removal from the airways of a patient. Using at least one flow unit, at least one respiratory airflow for an insufflation into the patient and at least one respiratory airflow for an exsufflation out of the patient are generated. The flow unit comprises at least one patient interface for connecting the patient to the respiratory therapy device and at least one respiratory air interface for connecting the respiratory therapy device to respiratory air and/or ambient air. In this case, the flow unit comprises at least two fans which are fluidically connected in parallel and are fluidically connected to at least one switchable valve unit. In this case, the valve unit is switched into at least one first valve position. In the first valve position, at least one first fan is fluidically connected to the patient interface and the respiratory air interface. The respiratory airflow for the insufflation or exsufflation is thus provided.

The method according to the invention also offers a particularly effective assistance during the secretion removal. A particularly rapid change between insufflation and exsufflation can take place by way of the switching over according to the invention of the valve unit and the switching in of the fan. The coughing process is thus assisted and/or simulated particularly well.

In the first valve position, at least one second fan is preferably at least partially and preferably completely fluidically separated from the patient interface and/or the respiratory air interface.

In one advantageous embodiment, the valve unit is preferably switched into at least one second valve position. In the second valve position, in particular at least one second fan is fluidically connected to the patient interface and the respiratory air interface. The respiratory airflow for the exsufflation is thus preferably provided if the respiratory airflow is provided for the insufflation in the first valve position. It is also possible that the respiratory airflow is thus provided for the insufflation if the respiratory airflow for the exsufflation is provided in the first valve position.

In the second valve position, the first fan is at least partially and preferably completely fluidically separated from the patient interface and/or the respiratory air interface.

The valve unit is preferably switched into at least one third valve position. In particular, the first fan and the second fan are at least partially and preferably completely fluidically separated from the patient interface and/or the respiratory air interface in the third valve position.

It is preferably possible to switch into intermediate positions in the first and/or second and/or third valve position.

The above-described respiratory therapy device is preferably operated as per the method according to the invention. The above-described respiratory therapy device is suitable and designed for the purpose in particular of being operated as per the method according to the invention.

The applicant reserves the right to claim a respiratory therapy device and in particular a coughing device which is used for the targeted assistance of a secretion removal from the airways of a patient and comprises at least one flow unit. The flow unit is used in particular for generating at least one respiratory airflow for an insufflation into the patient and in particular for generating at least one respiratory airflow for an exsufflation out of the patient. The flow unit comprises in particular at least one patient interface for connecting the patient to the respiratory therapy device. The flow unit comprises in particular at least one respiratory air interface for connecting the respiratory therapy device to respiratory air and/or ambient air. In this case, the flow unit is preferably suitable and designed for the purpose of setting at least one respiratory airflow for a respiration having at least one defined positive therapy pressure for assisting the exhalation procedure for a defined time by means of at least one fan and/or at least one valve unit following the respiratory airflow for the exsufflation.

Such a respiratory therapy device offers a recovery pause which is very pleasant for the patient between the coughing procedures.

The fan can be the above-described first or second fan in this case. The fan and/or the valve unit are preferably designed as described above.

BRIEF DESCRIPTION OF THE DRAWINGS

Further advantages and features of the present invention result from the description of the exemplary embodiments, which are explained hereafter with reference to the appended figures.

In the figures.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
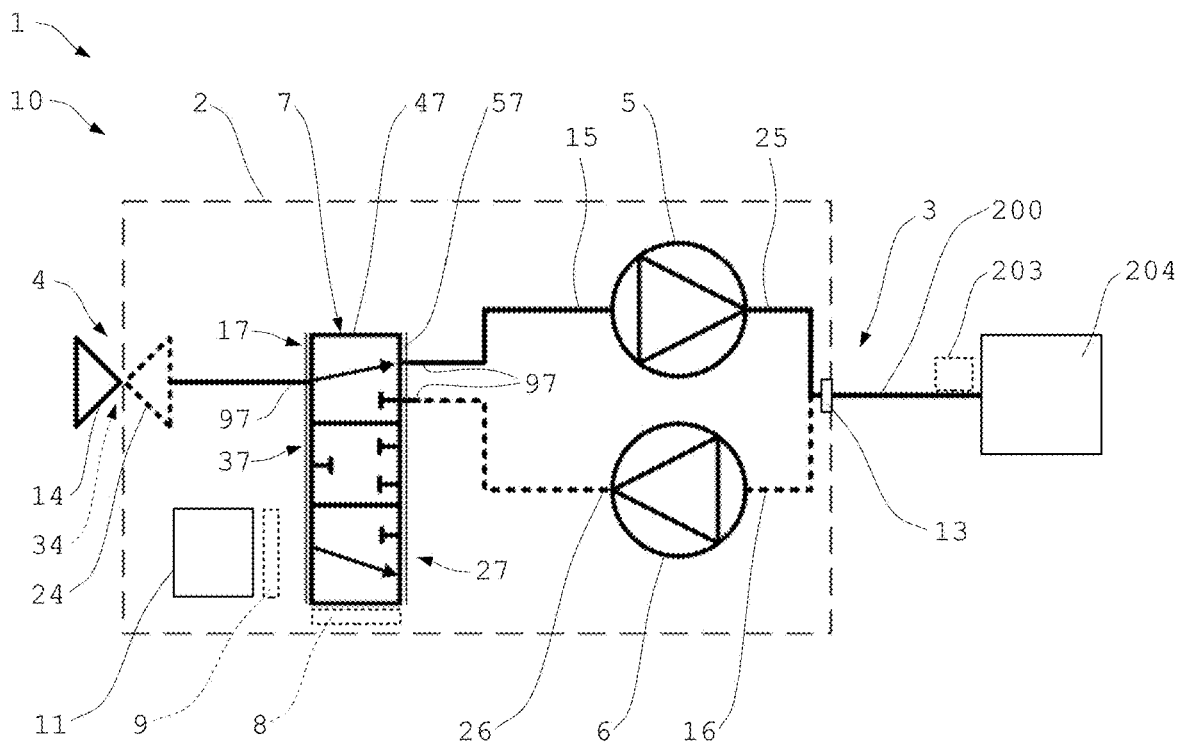
FIG. 1 shows a very schematic illustration of a respiratory therapy device according to the invention.

FIG. 1 shows a respiratory therapy device 1 according to the invention, which is designed as a coughing device 10. The respiratory therapy device 1 is operated here as per the method according to the invention and is used for the targeted assistance of a secretion removal from the airways of a patient.

The respiratory therapy device 1 comprises a flow unit 2, using which a respiratory airflow for an insufflation and a respiratory airflow for an exsufflation are generated. The flow unit 2 comprises a first fan 5, a second fan 6, a valve unit 7, and a patient interface 3 and also a respiratory air interface 4. The fans 5, 6 are connected in parallel and can be controlled separately. To control the valve unit 7 and the fans 5, 6, the respiratory therapy device 1 comprises a control unit 11 here.

The valve unit 7 comprises three fittings 97 here and offers three switchable valve positions 17, 27, 37. The valve unit 7 is designed as a 3/3-directional valve 47. Moreover, the valve unit 7 is designed here as a proportional valve 57, so that intermediate positions having various degrees of opening can be set in the valve positions 17, 27.

The first fan 5 is connected with an intake side 15 to a fitting 97 of the valve unit 7. The delivery side 25 or pressure side of the first fan 5 is connected here to the patient interface 3. The second fan 6 is connected with its delivery side 26 to a second fitting 97 of the valve unit 7. The intake side 16 of the second fan 6 is connected here to the patient interface 3. The valve unit 7 comprises a third fitting 97, which is connected here to the respiratory air interface 4.

The respiratory air interface 4 is fluidically connected to the surroundings of the respiratory therapy device 1, so that ambient air can be drawn in and used for the insufflation. For this purpose, the respiratory air interface 4 has an air inlet 14. Alternatively or additionally, the respiratory air interface 4 can also be connected to a respiratory gas source and, for example, a pressure bottle.

The respiratory air interface 4 is moreover equipped with an air outlet 24, via which the air drawn out during the exsufflation can be blown out into the surroundings of the device 1.

Air inlet 14 and air outlet 24 are preferably provided by a common opening 34, via which the air can be both drawn in and also blown out. Separate openings can also be provided for air inlet 14 and air outlet 24.

The patient interface 3 is equipped here with a coupling unit 13, to which a hose unit 200 can be coupled. The hose unit 200 is equipped with a patient interface 204. The patient interface 204 can be embodied, for example, as a full-face mask, a nasal mask, a nasal pillow, a mouthpiece, a tube, or as a larynx mask. Headgear can be provided for fixing the breathing mask 105.

The hose unit 200 shown here is only equipped with one breathing hose, via which the respiratory air both for the insufflation and also for the exsufflation is conveyed. For example, a single-hose system is provided, which is suitable for coughing maneuvers. Then, for example, breathing back into the hose unit 200 is possible. It is possible that a $CO_2$ washing in the region of the hose system is omitted. However, a two-hose system can also be coupled.

In one embodiment, the hose unit 200 can be equipped with a patient valve 203. Exhaled air can be continuously exhaustible via this, for example. The patient valve 203 can be designed, for example, as a passive exhalation system for $CO_2$ washing.

However, a patient valve 203 controllable by the respiratory therapy device can also be provided, so that the exhaust of exhaled air can be intentionally adapted to breathing phases or coughing phases, respectively.

The respiratory therapy device 1 preferably also comprises a sensor unit (not shown in greater detail here), which monitors the volume flow rate or flow and/or the pressure of the respiratory gas flow for the insufflation and/or exsufflation. For this purpose, the sensor unit can have corresponding pressure sensors and/or flow sensors. The control unit 11 can be suitable and designed for the purpose of setting and/or controlling the valve unit 7 and/or the fans 5, 6 as a function of the registered sensor signals. The patient valve 203 can also be controllable by the control unit 11.

The flow paths shown here can be equipped with at least one filter unit, to be able to provide a purified respiratory airflow.

In one advantageous embodiment, the respiratory therapy device 1 can also be equipped with a respiration unit 9. The respiration unit 9 is then operationally connected to the flow unit 2, to thus generate a respiratory airflow for the respiration of the patient. For this purpose, the respiration unit 9 can control at least one of the fans 5, 6 and/or the valve unit 7 accordingly. The respiration unit 9 is preferably also operationally connected to the control unit 11 and the sensor unit.

In one embodiment of the respiration unit 9, at least one piece of software is stored for this purpose in the control unit 11, on the basis of which the flow unit 2 is controlled. This offers a particularly advantageous design expenditure. The respiration unit 9 can also have an independent or separate control unit.

The respiratory therapy device 1 can also be equipped with an oscillator unit, in order to apply a defined oscillation to the respiratory airflow for the insufflation and exsufflation. For example, the oscillator unit 8 is provided by the valve unit 7. Such an embodiment is described in greater detail with reference to FIGS. 5 to 10.

The respiratory therapy device 1 can have further components (not shown in greater detail here). For example, a display unit or a display screen and an operating unit for carrying out inputs and settings can be provided. Moreover, the respiratory therapy device 1 can have at least one communication interface, via which it can communicate in a wireless and/or wired manner with external devices. Moreover, a remote control can also be provided for the respiratory therapy device 1. Such components are preferably operationally connected to the control unit 11.

Specifications for the control of the valve unit 7 and/or the fans 5, 6 are preferably stored or saved in the control unit 11. These specifications can in particular be at least partially adapted by the user and/or a caregiver. The control unit 11 comprises, for example, at least one controller and/or other control components.

The valve unit 7 is shown here in the first valve position 17. In this case, the first fan 5 is connected on its intake side 15 to the respiratory air interface 4. The first fan 5 can thus draw in air from the surroundings of the device 1 and provide it as the respiratory airflow for the insufflation at the patient interface 3. From there, the respiratory airflow can then be blown via the hose unit 200 and the patient interface 204 into the patient for insufflation.

The second fan 6 can be activated or also deactivated in the first valve position 17. Since the second fan 6 is blocked in relation to the respiratory air interface 4 in the first valve position 17, no undesired exsufflation occurs during the provided insufflation even upon operation of the fan 6. The second fan 6 can thus already be ramped up to a particularly favorable speed for the imminent exsufflation during the insufflation.

This advantage is also provided in the second valve position 27. The first fan 5 can then be brought to a desired speed without impairing the exsufflation carried out using the second fan 6.

In the second valve position 27, the delivery side 26 of the second fan 6 is connected here to the respiratory air interface 4. The second fan 6 can draw air out of the patient via the patient interface 3 and the hose unit 200 coupled thereon and also the patient interface 204 during the exsufflation. The second fan 6 then blows out the drawn-out air via the respiratory air interface 4 in the surroundings of the device 1.

In the third valve position 37, neither of the fans 5, 6 is connected here to the respiratory air interface 4 and/or both fans 5, 6 are blocked.

Figure 2:
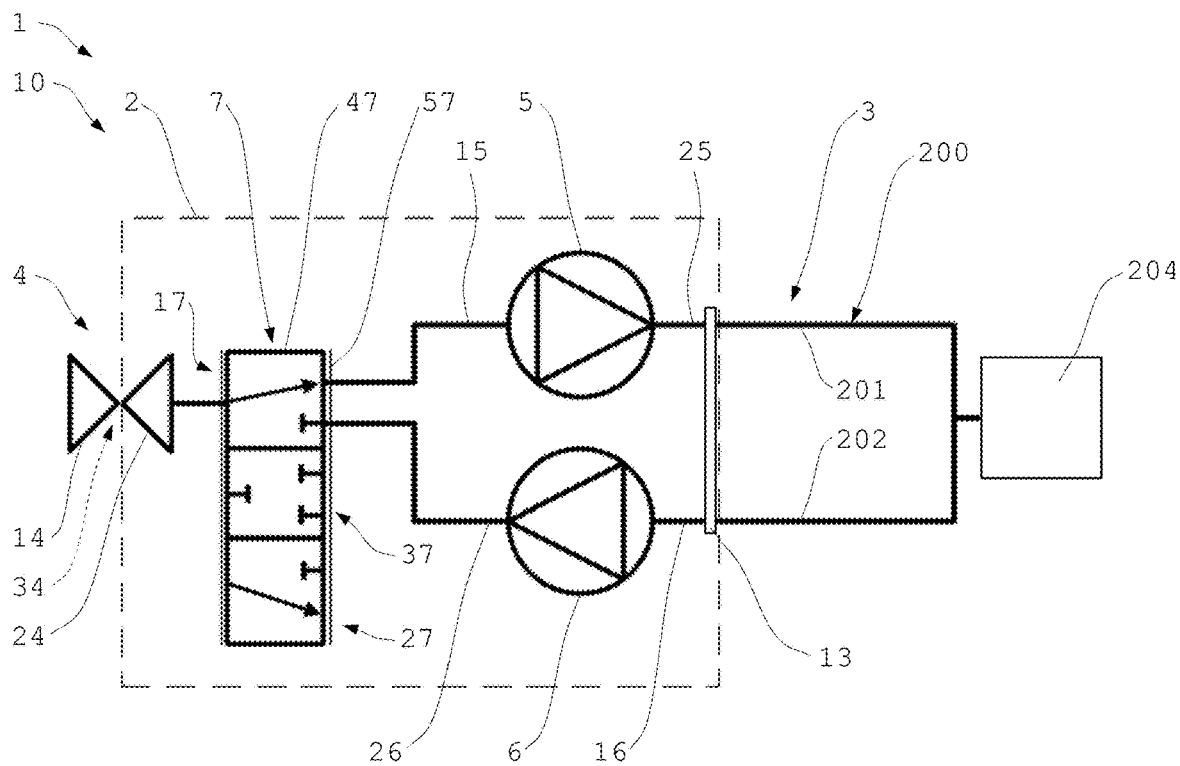
FIG. 2 shows a very schematic illustration of a further respiratory therapy device.

The respiratory therapy device 1 is shown with an alternatively embodied patient interface 3 in FIG. 2. The patient interface 3 is equipped here with a coupling unit 13, to which a hose unit 200 having two hoses is connectable.

For this purpose, the hose unit 200 is equipped here with an inhalation hose 201 and an exhalation hose 202, which are coupled to the patient interface 204. The inhalation hose 201 is coupled here to the first fan 5, so that the respiratory airflow for the insufflation can flow via this. The exhalation hose 202 is coupled here to the second fan 6, so that the respiratory airflow for the exsufflation can flow via this. For example, the patient interface 104 comprises a patient-proximal Y-piece. The two hoses 201, 202 can be connected there.

Such a two-hose system can also be used particularly well for the respiration. This is particularly advantageous if the respiratory therapy device 1 is also equipped with a respiration unit 9. This is also particularly advantageous if the $CO_2$-rich exhaled air is not to be inhaled again.

Such an embodiment of the respiratory therapy device 1 having a two-hose system is particularly advantageous in this aspect: to conduct the respiratory air during an insufflation/inhalation toward the patient through the hose connection 201 and during an exsufflation/exhalation away from the patient through the hose connection 202, almost no $CO_2$-rich respiratory air is inhaled again. The integrated valve unit alone controls the flow direction and through flow of the hose connections as a function of the breathing phases in this case, without an additional patient valve having to be used. This is a particular advantage of the invention, which results in particular due to the two fans connected in parallel and/or the switchable valve unit coupled thereon.

Figure 3:
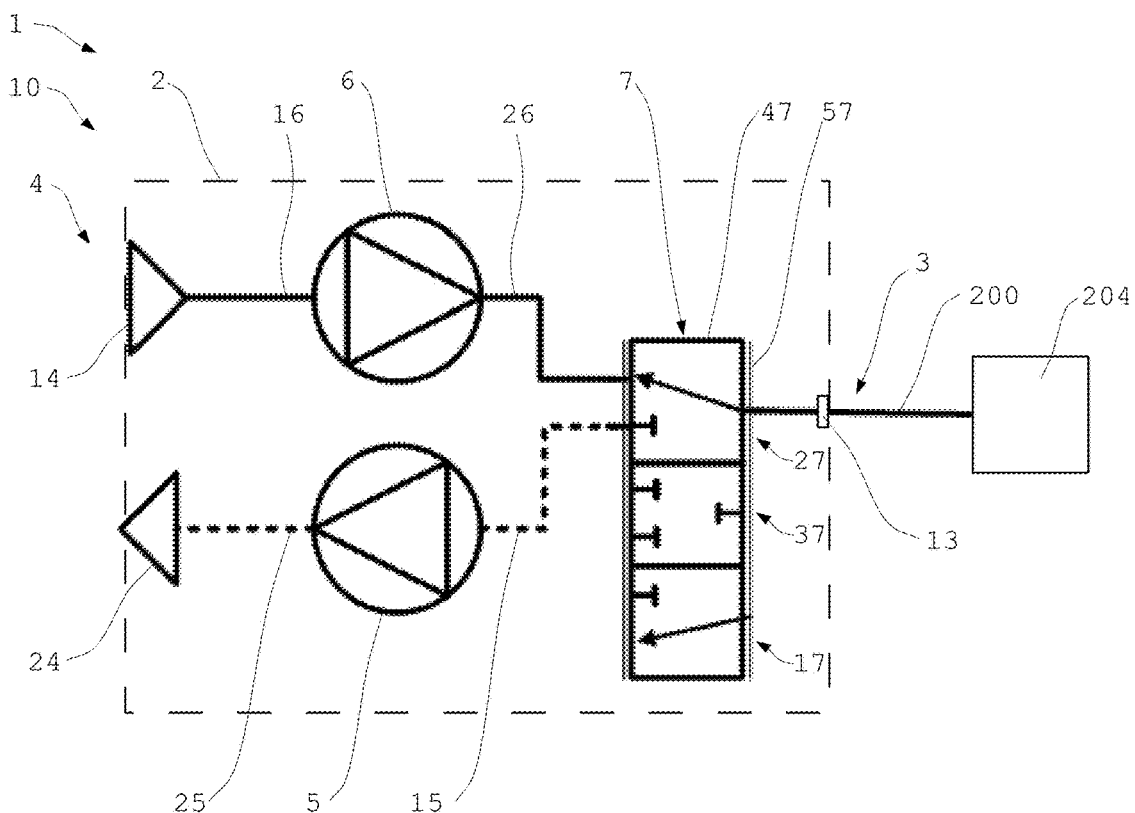
FIG. 3 shows a very schematic illustration of another respiratory therapy device.

FIG. 3 shows an alternative embodiment of the respiratory therapy device 1. The valve unit 7 is arranged here between the fans 5, 6 and the patient interface 3. In this case, the intake side 15 of the first fan 5 is connected to the valve unit 7. The delivery side 25 of the first fan 5 is connected here to an air outlet 24 of the respiratory air interface 4. Thus, either the first fan 5 or the second fan 6 can be connected to the patient interface 3 by means of the valve unit 7.

The second fan 6 is connected with its delivery side 26 to the valve unit 7. The intake side 16 of the second fan 6 is connected here to an air inlet 14 of the respiratory air interface 4. While two of the fittings 97 are thus coupled to the fans 5, 6, the third fitting 97 is connected here to the patient interface 3.

The valve unit 7 is located here in the second valve position 27. In this case, the second fan 6 is connected to the patient interface 3. The fan 6 can thus draw in the air via the air inlet 14 and blow it via the patient interface 3 and the hose unit connected thereto and/or the patient interface 204 into the patient for the insufflation. The first fan 5 is blocked off in relation to the patient interface 3 in this valve position 27.

In the second valve position 27, the first fan 5 can be operated further, without undesired exsufflation occurring. The first fan 5 can thus already be ramped up to an optimum speed, which is required for the next exsufflation, during the insufflation, for example.

In the first valve position 17, the first fan 5 is connected here to the patient interface 3. The second fan 6 is then blocked off from the patient interface 3. The first fan 5 then generates a respiratory airflow for the exsufflation and draws air via the patient interface 3 and/or the hose unit 200 and the patient interface 204 out of the patient for this purpose. The first fan 5 blows out the air via the air outlet 24 from the device 1 into the surroundings. The first valve position 17 enables an adaptation of the speed of the second fan 6, without unfavorably impairing the exsufflation.

Figure 4:
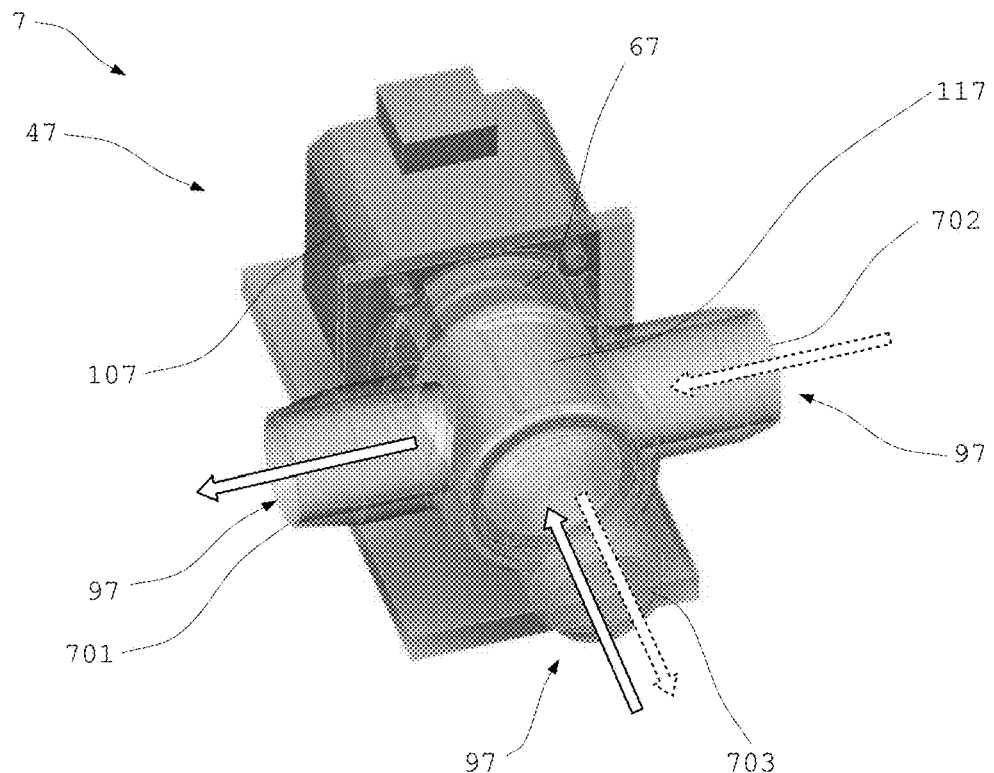
FIG. 4 shows a schematic illustration of a valve unit in a perspective view.

FIG. 4 shows an embodiment of the valve unit 7 as a rotary slide valve 67. The rotary slide valve 67 is a 3/3-directional valve 47 here and can be used as a proportional valve 57.

The rotary slide valve 67 comprises three fittings 97 here and can be moved into three valve positions. The valve positions correspond, for example, to the valve positions 17, 27, 37 shown in FIG. 1 or FIG. 3. Thus, either the first fan 5 or the second fan 6 can be connected to the respiratory air interface 4 and/or the patient interface 3 using the valve unit 7.

A rotatable valve piston 117 is provided here for switching the valve positions, which is moved by means of a drive unit 107 into the respective position. For better illustration of the rotating piston 117, the valve unit 7 is shown partially transparent here.

The rotary slide valve 67 shown here can be used, for example, in the flow unit 2 described with reference to FIG. 1.

The intake side 15 of the first fan 5 is then connected to a first fitting 701. The delivery side 26 of the second fan 6 is connected to a second fitting 702. The respiratory air interface 4 is connected with the air inlet 14 or the air outlet 24 to a third fitting 703. Thus, either the first fan 5 or the second fan 6 can be connected to the respiratory air interface 4 by rotating the valve piston 117.

In the position of the valve piston 117 shown here, the first fan 5 is switched in, so that an insufflation can occur. If the valve piston 117 is rotated accordingly, the second fan 6 can blow out the air via the respiratory air interface 4, so that an exsufflation is possible. The respiratory airflow for the insufflation is indicated here by two arrows having solid lines. The respiratory airflow for the exsufflation is indicated here by dashed arrows.

If the rotary slide valve 67 shown here is used in the flow unit 2 according to FIG. 3, the assignment of the fittings 97 changes accordingly. The delivery side 25 of the first fan 5 is then connected to the first fitting 701. In the setting shown here of the valve piston 117, an exsufflation is then provided. The intake side 16 of the second fan 6 is then connected to the second fitting 702. The patient interface 3 is connected to the third fitting 703.

The functioning of the valve unit 7 shown in FIG. 4 is explained by way of detail hereafter. For this purpose, various valve positions are shown in FIGS. 5 to 9. The valve unit 7 is shown in a sectional front view looking toward the valve piston 117.

The rotary slide valve 67 shown here can assume various intermediate positions 77, 87 having different degrees of opening by pivoting the valve piston 117 in the first and second valve positions 17, 27. In this case, arbitrary and/or discrete intermediate positions are possible. Continuous and/or fixedly specified intermediate positions can also be provided. The valve unit 7 can thus assume intermediate positions for the insufflation and exsufflation, in which the flow is reduced accordingly by a cross-sectional reduction of the flow path.

Figure 5:
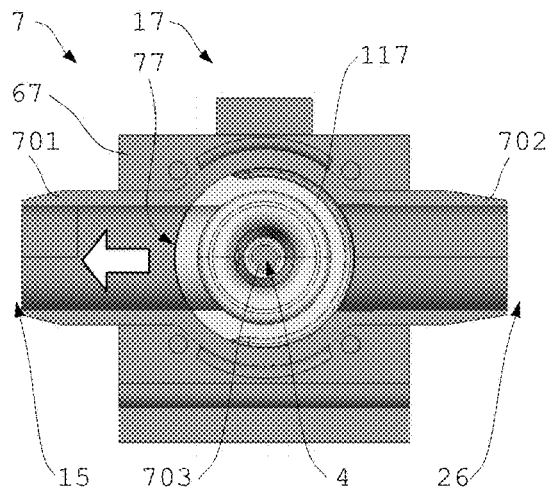
FIG. 5-9 show schematic illustrations of the valve unit in various settings in a sectional view.
Figure 6:
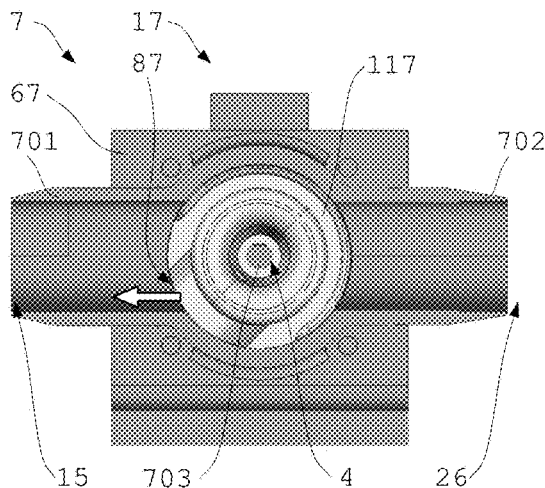

FIG. 5 and FIG. 6 show the valve unit 7 in the first valve position 17. In this case, the valve unit 7 of FIG. 5 is shown in a completely open valve position 77 and in FIG. 6 it is shown in a partially closed valve position 87.

Figure 7:
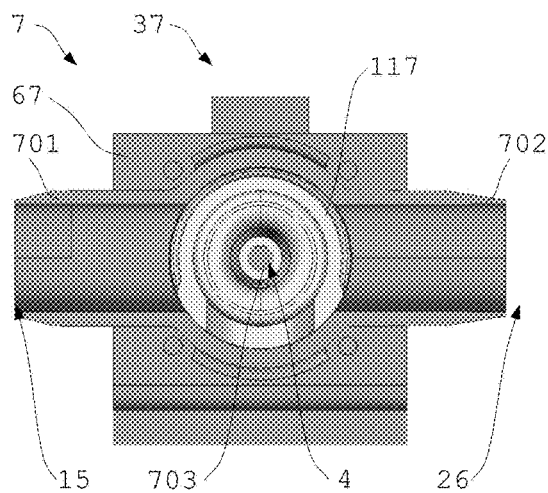

FIG. 7 shows the valve unit 7 in the third valve position 37. The fittings 97 are blocked here.

Figure 8:
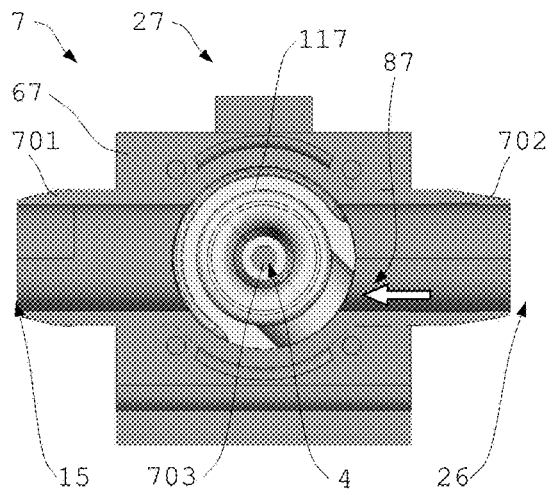
Figure 9:
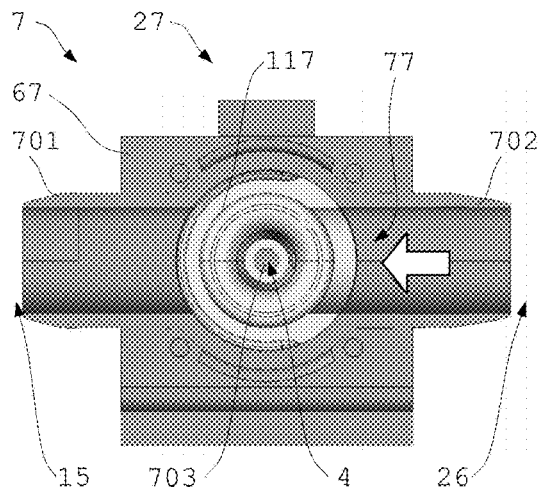

In FIG. 8 and FIG. 9, the valve unit 7 is shown in the second valve position 27. In this case, FIG. 8 shows a partially open valve position 87 and FIG. 9 shows a completely open valve position 77.

If the valve unit 7 shown here is used in the flow unit 2 described with reference to FIG. 1, the intake side 15 of the first fan 5 is connected to the first fitting 701. The delivery side 96 of the second fan is connected to the second fitting 702. The respiratory air interface 4 is connected to the third fitting 703.

A maximum flow for the insufflation can then be achieved with the completely open valve position 77 of FIG. 5. The flow path between the first fan 5 and the respiratory air interface 4 is maximally enabled here.

The only partially open valve position 87 of FIG. 6 enables a correspondingly reduced flow for the insufflation. The flow path between the first fan 5 and the respiratory air interface 4 is intentionally restricted here.

In the third valve position 37 shown in FIG. 7, neither an insufflation nor an exsufflation takes place. Both fans 5, 6 are separated from the respiratory air interface 4.

The partially open valve position 87 in the second valve position 27 shown in FIG. 8 enables a restricted or reduced exsufflation. The flow path between second fan 6 and the respiratory air interface 4 is only partially enabled here.

The connection between second fan 6 and respiratory air interface 4 is maximally enabled in FIG. 9, so that a maximum respiratory airflow can be set for the exsufflation.

In the event of an integration of the rotary slide valve 67 into the flow unit 2 described in FIG. 3, the connection of the fittings 701, 702, 703 is modified accordingly as per the interconnection shown in FIG. 3.

The rotary slide valve 67 presented here can also be used for the targeted generation of an oscillation of pressure and/or flow of the respiratory airflow. For this purpose, the valve piston 117 is pivoted between various settings at a predefined or settable frequency.

The valve positions shown in FIG. 5 to FIG. 8 can be assumed, for example, to generate an oscillation during the insufflation.

For example, firstly the completely open valve position 77 shown in FIG. 5 is provided. Thus, initially a maximum possible positive pressure or maximum possible flow is provided during the insufflation. Subsequently, the valve piston 117 is pivoted into the partially open valve position 87 shown in FIG. 6. A targeted reduction of the pressure or flow thus occurs during the insufflation.

Subsequently, the valve piston 117 is moved into the closed valve position 37 shown in FIG. 7. A respiratory airflow having a flow of essentially zero thus results during the insufflation. The pressure applied to the patient interface 204 can sink to a level in this case, for example, which is essentially determined by the degree of lung filling.

Subsequently, the valve piston 117 is pivoted into the partially open valve position 87 of the second valve position 27 shown in FIG. 8. The delivery side 26 of the second fan 6 provided for the exsufflation is thus switched in. A desired short-term reduction of the pressure with a flow reversal during the oscillation thus occurs in this setting.

A directional reversal of the rotational movement of the valve piston 117 preferably now follows. In this case, the valve piston 117 is rotated back into the above-described settings in reverse sequence, until the completely open valve position 77 of the first valve position 17 is reached in FIG. 5.

The above-described valve movement then takes place again. The repetition rate can be, for example, between 1 Hz and 30 Hz in this case.

The generation of an oscillation during the exsufflation can be achieved, for example, by the valve positions shown in FIG. 6 to FIG. 9.

For example, the valve piston 117 is firstly arranged in the completely open valve position 77 of the second valve position shown in FIG. 9. This enables an exsufflation with a maximum possible negative pressure and/or a maximum flow for the exsufflation.

The valve body 117 is subsequently pivoted into the only partially open valve position 87 of FIG. 8. The flow is thus intentionally reduced during the exsufflation.

The valve piston 117 is then moved into the third valve position 37 of FIG. 7. The flow paths for exsufflation and insufflation are then completely closed. The flow is substantially zero. The pressure applied to the patient interface 204 can rise to a level, for example, which is essentially determined by the degree of lung filling.

The valve piston 117 is subsequently pivoted into the partially open valve position 87 of the first valve position 17, as shown in FIG. 6. The intake side 15 of the first fan 5 is thus intentionally switched in during the exsufflation. A desired short-term increase of the pressure with a corresponding flow reversal thus occurs during the oscillation.

The valve piston 117 is subsequently pivoted back again via the above-described positions in reverse sequence.

If the valve piston 117 reaches the position shown in FIG. 9, the rotational movement begins from the beginning during the exsufflation. The reversal of the rotational movement preferably also takes place at a frequency of 1 Hz to 30 Hz.

The rotational movement during the oscillation preferably takes place between an end position fully open and at least partially closed. The rotational movement during the oscillation can also occur between the two end positions each fully open, however. The rotational movement during the oscillation preferably occurs between the end positions fully open for one flow direction and partially open in the other flow direction. A greater dissipation of the pressure can thus be ensured during the insufflation, for example. The specifications of the rotational direction relate in this case in particular to one flow direction. Moreover, an end position is understood in particular as an effective end position. The effective end position can correspond to a stop. The effective end position can be independent of an end stop, for example, in a valve without stop or a 360° valve.

Valve positions other than those shown here can also be provided for the oscillation during the insufflation and/or exsufflation.

Figure 10:
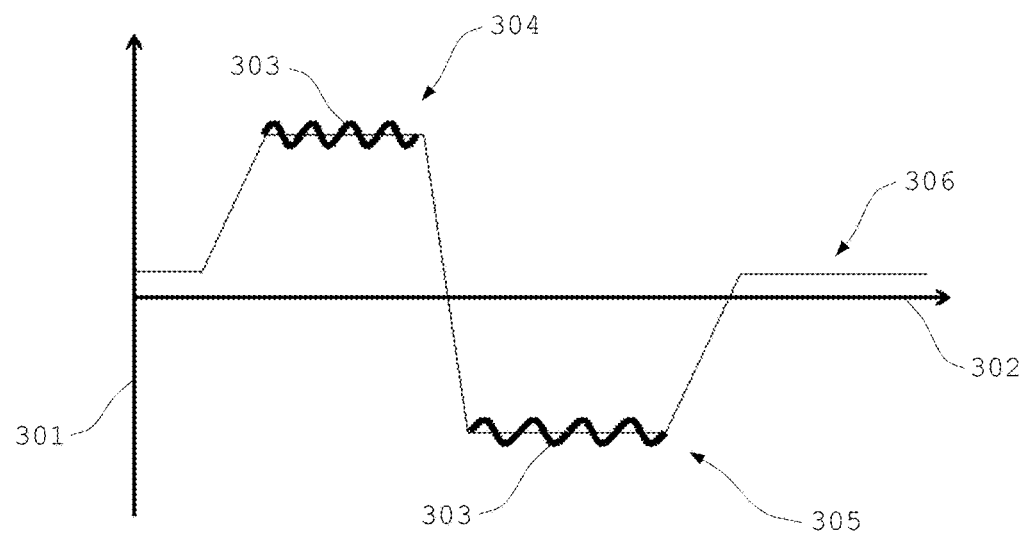
FIG. 10 shows a very schematic diagram of the functionality of the respiratory therapy device.

FIG. 10 shows an example of a pressure curve as can be provided during a usage of the respiratory therapy device 1. For this purpose, the pressure 301 was plotted against the time 302.

During the insufflation 304, a correspondingly high pressure 301 is provided for a defined time. For a particularly effective stimulation of the coughing reflex and/or for particularly effective detaching of the secretion, it then switches over very briefly to the exsufflation 305. For this purpose, the pressure 301 is lowered within a defined time span to a correspondingly negative level and kept there for a specific duration.

A renewed increase of the pressure to the desired level for the insufflation can then be performed, for example. A very rapid reduction of the pressure 301 is subsequently performed again for the exsufflation. This alternation between insufflation and exsufflation can be repeated for a desired time span. For example, the number of the repetitions and/or the frequency of the repetitions can be specified by a user and/or caregiver.

In the curve shown here, a pause 306 is provided after the exsufflation 305. This offers a great relief to the patient, since the coughing processes require a substantial physical exertion. The pressure curve shown here has a slight overpressure or a positive therapy pressure during the pause 306. The exhalation against such a slight, intentional overpressure is particularly reasonable for respiratory therapy. The overpressure can be formed, for example, as a constant positive pressure (CPAP).

The pressure is between 4 and 30 mbar, for example. In contrast, a pressure in the range of approximately +/−70 mbar or even higher can be set for the exsufflation and/or insufflation. In the pause, substantially smaller flows typically result in the scope of inhalation and exhalation in comparison to the insufflation or exsufflation.

A respiration can also be provided in the pause. The respiration unit 9 is then active in particular. For example, a pressure up to approximately 50 mbar and in particular between 10-35 mbar is then provided for the respiration or inspiration.

The drop of the pressure 301 at the transition from insufflation to exsufflation preferably occurs here by way of correspondingly rapid switching over of the valve unit 7. The speed of the fan 6 for the exsufflation is preferably adapted accordingly even before the switching procedure of the valve unit 7. However, this is not necessary according to the invention.

The rise of the pressure 301 from the exsufflation to the next insufflation or after a pause toward the following insufflation preferably occurs less rapidly or over a longer time span. The pressure rise can be performed by a correspondingly cautious ramping up of the corresponding fan 5, 6, in addition to the change of the valve position.

The increase of the pressure 301 in preparation for the pause 306 is also performed here by a correspondingly slow speed increase of the fan 5.

Figure 11:
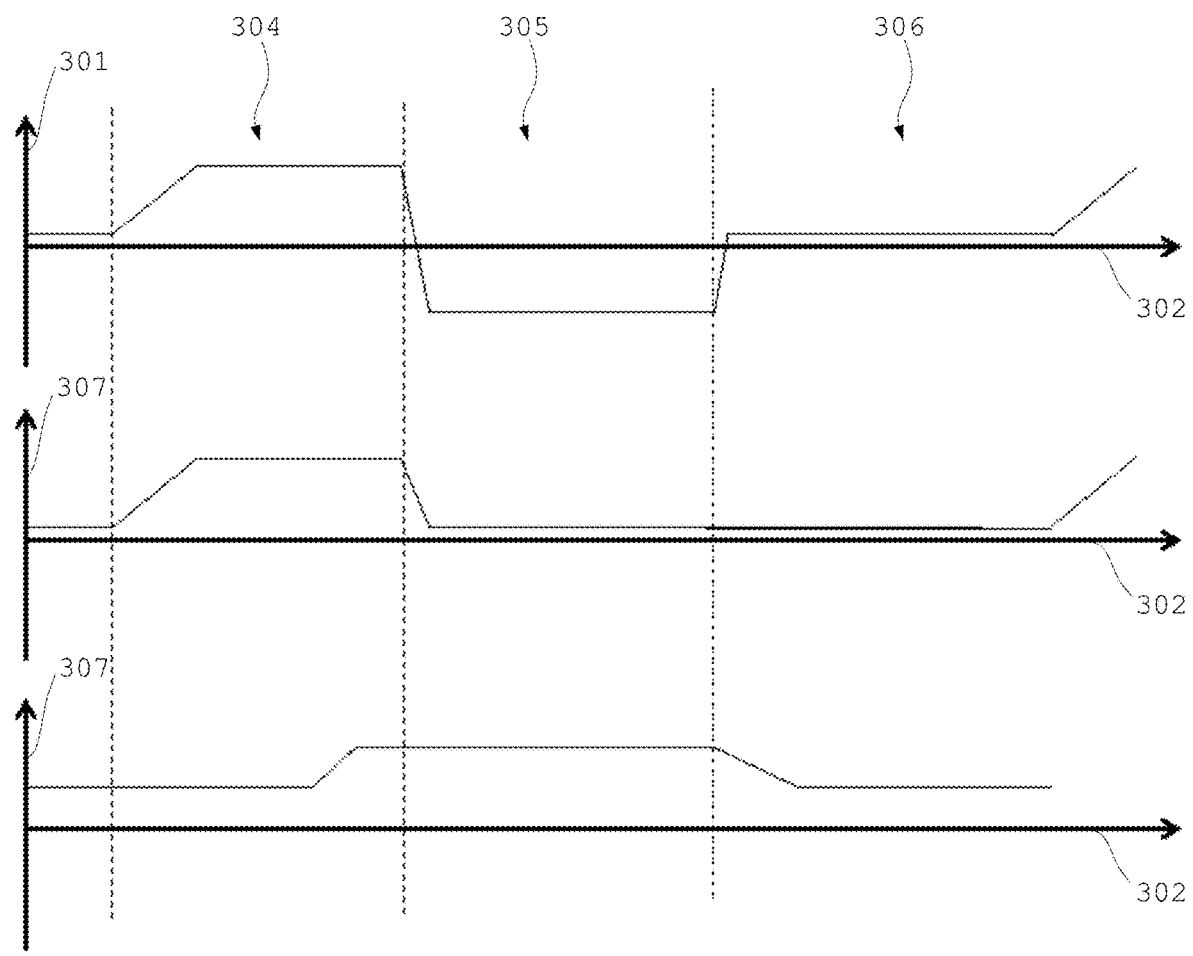
FIG. 11 shows a further very schematic diagram of the functionality of the respiratory therapy device.

FIG. 11 shows an example of a coughing maneuver having a subsequent pause 306. For this purpose, the pressure 301 was plotted against the time 302 in the upper graphic. In the middle graphic, a speed 307 of the first fan 5 was plotted by way of example and in very idealized form against the time 302. In the lower graphic, a speed 307 of the second fan 6 was plotted by way of example and in very idealized form against the time 302. The vertically extending, dashed lines very schematically indicate switching over of the valve position in this case.

At the beginning of the maneuver, the valve unit 7 is moved into the valve position for the insufflation. According to the embodiment shown in FIG. 1, the first valve position 17 is assumed for this purpose, so that the first fan 5 is switched in.

The speed 307 of the first fan 5 is then increased slowly over a defined time. The pressure 301 increases accordingly. After reaching the pressure 301 required for the insufflation, the speed 307 is maintained.

After a specific time, the change takes place from the insufflation 304 to exsufflation 305. The change occurs particularly rapidly here for an effective triggering of the coughing reflex and/or for a particularly effective assistance of the secretion removal. For this purpose, the valve unit 7 is switched into the second valve position 27. The pressure 301 drops accordingly over a very short time span. The negative pressure 101 necessary for the exsufflation 305 is reached.

To be able to enable the pressure transition particularly rapidly, the speed 307 of the second fan 6 was increased to the required amount already before the switching in. The pressure 301 and the speed 107 for the exsufflation 305 are now maintained for a predetermined time 102. The second fan 6 thus reaches its target operating range before the switchover into the exsufflation phase.

A switchover of the valve unit 7 into the first valve position subsequently takes place again. The first fan 5 is thus switched in again. After the switching in, the speed 307 of the first fan 5 is increased enough that a correspondingly lighter overpressure suitable for the respiration during the pause 306 is provided. The first fan 5 thus accelerates during the pressure buildup or to generate the pressure curve. The second fan 6 is now no longer switched in, so that its speed 107 can be reduced accordingly.

After the end of the pause 306, an increase of the speed 107 of the first fan 5 can again take place, to reach the pressure 301 required for the insufflation 304. The coughing maneuver can now begin from the beginning.

Overall, the invention presented here offers the advantage that a particularly patient-friendly and also effective coughing machine is provided. Moreover, the invention offers the advantage that substantially improved respiration is also possible. A particularly gentle assistance during the secretion removal can thus take place during the respiration, for example, by the patient being assisted in an exhalation phase using a negative therapy pressure. The invention can particularly advantageously be used in this case with a two-hose system.

A further advantage is that the respiration can take place alone or also in combination with a coughing and/or secretion therapy. For example, a pause takes place during a coughing and/or secretion therapy, in which a positive therapy pressure is used to relieve the patient. A respiration of the patient can also take place in the pause.

| List of reference numerals: | |
|---|---|
| 1 | respiratory therapy device |
| 2 | flow unit |
| 3 | patient interface |
| 4 | respiratory air interface |
| 5 | fan |
| 6 | fan |
| 7 | valve unit |
| 8 | oscillator unit |
| 9 | respiration unit |
| 10 | coughing device |
| 11 | control unit |
| 13 | coupling unit |
| 14 | air inlet |
| 15 | intake side |
| 16 | intake side |
| 17 | valve position |
| 24 | air outlet |
| 25 | delivery side |
| 26 | delivery side |
| 27 | valve position |
| 34 | opening |
| 37 | valve position |
| 47 | directional valve |
| 57 | proportional valve |
| 67 | rotary slide valve |
| 77 | valve position |
| 87 | valve position |
| 97 | fitting |
| 107 | drive |
| 117 | valve piston |
| 200 | hose unit |
| 201 | inhalation hose |
| 202 | exhalation hose |
| 203 | patient valve |
| 204 | patient interface |
| 301 | pressure |
| 302 | time |
| 303 | oscillation |
| 304 | insufflation |
| 305 | exsufflation |
| 306 | pause |
| 307 | speed |
| 701 | fitting |
| 702 | fitting |
| 703 | fitting |

What is claimed is:

1. A respiratory therapy device for the targeted assistance of a secretion removal from the airways of a patient, wherein the device comprises a flow unit for generating at least one respiratory airflow for an insufflation into the patient and for generating at least one respiratory airflow for an exsufflation out of the patient, which flow unit comprises a patient interface for connecting the patient to the respiratory therapy device and a respiratory air interface for connecting the respiratory therapy device to respiratory air or ambient air, and wherein the flow unit comprises at least two flow paths extending in parallel, wherein each flow path comprises at least one gas source each having at least one intake side and at least one delivery side, a first gas source being fluidically coupled with its intake side and a second gas source being fluidically coupled with its delivery side to a switchable valve unit which is fluidically arranged between each of the first gas source and the second gas source and the respiratory air interface.

2. The respiratory therapy device of claim 1, wherein the first and second gas sources are designed as electronically operated fans.

3. The respiratory therapy device of claim 2, wherein the fans are arranged inversely in relation to one another in the flow paths.

4. The respiratory therapy device of claim 2, wherein the valve unit is configured for connecting the at least one intake side of a first fan to the respiratory air interface or to the patient interface and blocking the at least one delivery side of a second fan in at least one valve position.

5. The respiratory therapy device of claim 2, wherein the valve unit is configured for blocking the at least one intake side of a first fan and connecting the at least one delivery side of a second fan to the respiratory air interface or to the patient interface in at least one valve position.

6. The respiratory therapy device of claim 2, wherein the valve unit is configured for blocking the at least one intake side of a first fan and blocking the at least one delivery side of a second fan in at least one valve position.

7. The respiratory therapy device of claim 1, wherein the valve unit comprises at least one 3/3-directional valve.

8. The respiratory therapy device of claim 1, wherein the valve unit is designed as a proportional valve.

9. The respiratory therapy device of claim 1, wherein the valve unit comprises at least one rotary slide valve.

10. The respiratory therapy device of claim 2, wherein the flow unit is configured for operating at least one of the at least two fans even if the at least one intake side or the at least one delivery side of a fan is blocked by the valve unit and/or is configured for setting a requested speed of at least one of the at least two fans while the at least one intake side or the at least one delivery side of a fan to be set is blocked by the valve unit.

11. The respiratory therapy device of claim 1, wherein the device further comprises at least one oscillator unit for applying at least one defined oscillation to the respiratory airflow for the insufflation and/or exsufflation.

12. The respiratory therapy device of claim 11, wherein the oscillator unit is configured for generating the at least one defined oscillation by repeated switching over of the valve unit and/or is configured for switching over the valve unit between a fully open valve position and a partially open valve position during insufflation and/or exsufflation.

13. The respiratory therapy device of claim 11, wherein the oscillator unit is configured for switching over the valve unit between an at least partially open valve position for insufflation and an at least partially open valve position for exsufflation during insufflation and/or for switching over the valve unit between an at least partially open valve position for exsufflation and an at least partially open valve position for insufflation during the exsufflation.

14. The respiratory therapy device of claim 11, wherein the oscillator unit is configured for setting a different maximum and/or minimum degree of opening of the valve unit during insufflation than during exsufflation and/or is configured for switching over the valve unit at a frequency of 0.1

Hz to 100 Hz and/or is configured for setting a different frequency and/or amplitude for insufflation than for exsufflation.

15. The respiratory therapy device of claim 1, wherein the respiratory air interface comprises at least one air inlet and at least one air outlet, the at least one air inlet and the at least one air outlet being provided by a common opening.

16. The respiratory therapy device of claim 1, wherein the patient interface comprises at least one coupling unit for connecting at least one hose unit, which hose unit is connectable to at least one breathing opening of the patient and which comprises at least one inhalation hose and at least one exhalation hose or which comprises only at least one inhalation hose.

17. A respiratory therapy device for assisting a secretion removal from the airways of a patient, wherein the device comprises a flow unit for generating at least one respiratory airflow for an insufflation into the patient and for generating at least one respiratory airflow for an exsufflation out of the patient, which flow unit comprises a patient interface for connecting the patient to the respiratory therapy device and a respiratory air interface for connecting the respiratory therapy device to the respiration air or breathing air and further comprises at least two flow paths, each flow path comprising at least one gas source having in each case at least one intake side and at least one delivery side, which gas sources are fluidically coupled to a switchable valve unit which is fluidically arranged between the flow unit and the respiratory air interface.

18. The respiratory therapy device of claim 1, wherein the flow unit is configured for setting at least one respiratory airflow for a respiration having at least one defined dynamic pressure for assisting the exhalation procedure for a defined time following a respiratory airflow for the exsufflation.

19. The respiratory therapy device of claim 1, wherein the device further comprises at least one respiration unit which is configured for generating a respiratory airflow for the respiration of the patient by the flow unit.

20. The respiratory therapy device of claim 1, wherein the device further comprises a sensor unit which monitors a volume flow rate or flow and/or a pressure of a respiratory gas flow for the insufflation and/or exsufflation, and a control unit which is configured for setting or controlling the switchable valve unit and the first and second gas sources as a function of signals from the sensor unit.

* * * * *